United States Patent [19]

Amatsu et al.

[11] Patent Number: 5,780,677
[45] Date of Patent: Jul. 14, 1998

[54] PROCESS FOR PRODUCING GLUTAMINE DERIVATIVE

[75] Inventors: Kazumi Amatsu; Yoshiyuki Yamada; Yoshikazu Mori; Shoichi Mizutaki, all of Osaka; Masaji Kasai, Kanagawa; Shinji Tomioka, Wakayama, all of Japan

[73] Assignee: Kyowa Hakko Kogyo Co., Ltd., Japan

[21] Appl. No.: 833,001

[22] Filed: Apr. 4, 1997

Related U.S. Application Data

[63] Continuation of Ser. No. 418,469, Apr. 7, 1995, abandoned.

[30] Foreign Application Priority Data

Apr. 18, 1994 [JP] Japan ............................. 6-078718

[51] Int. Cl.$^6$ .................................................. C07C 229/00
[52] U.S. Cl. ........................................................ 562/561
[58] Field of Search ................................. 562/571, 561

[56] References Cited

U.S. PATENT DOCUMENTS 3,206,506  9/1965  Griffith .

5,380,934  1/1995  Inoue ................................. 562/561

FOREIGN PATENT DOCUMENTS 63-51399  3/1988  Japan .

OTHER PUBLICATIONS

Hoppe–Seyler's Z. Physiol. Chem., 105, 58 (1919), Thierfelder et al.
J. National Cancer Inst., 7, 275 (1947), "Studies on the Effect of Pyruvate on the Desamidation et al" Price et al pp. 275–279.
Aust. J. Chem., 7, 173 (1954).

*Primary Examiner*—Michael L. Shippen
*Attorney, Agent, or Firm*—Nixon & Vanderhye

[57] ABSTRACT

N-chloroacetylglutamine is produced by reacting chloroacetyl chloride with an alkaline aqueous solution of glutamine the presence of a water-immiscible organic solvent, separating an aqueous layer by liquid-liquid separation, and crystallizing N-chloroacetyl-glutamine from the aqueous layer under acidic conditions. N-Chloroacetylglutamine useful as an intermediate for producing glycyl-L-glutamine which has higher stability than L-glutamine and is used as a component of an infusion solution can be obtained with high efficiency at low cost.

1 Claim, No Drawings

PROCESS FOR PRODUCING GLUTAMINE DERIVATIVE

This is a Rule 62 File Wrapper Continuation of application Ser. No. 08/418,469, filed 07 Apr. 1995, now abandoned.

FIELD OF THE INVENTION

This invention relates to a process for producing N-chloroacetylglutamine useful as an intermediate for synthesizing glycylglutamine. Glycyl-L-glutamine has higher stability and higher water-solubility than L-glutamine, and is used as a component of an infusion solution.

BACKGROUND OF THE INVENTION

It is known that N-chloroacetylglutamine is prepared by reacting chloroacetyl chloride with glutamine by the Schotten-Baumann reaction.

Known techniques for purifying N-chloroacetyl-glutamine include extraction using an organic solvent (Hoppe-Seyler's Z. Physiol. Chem., 105, 58 (1919) and J. National Cancer Inst., 7, 275 (1947)). However, this purification technique is not suitable for industrial production because of low yield and complicated processing operations involved.

N-Chloroacetyl-L-glutamine is difficult to purify because of its water solubility and sensitivity to heat. If unpurified N-chloroacetyl-L-glutamine is treated with aqueous ammonia to give glycyl-L-glutamine, high purity glycyl-L-glutamine cannot be obtained due to difficulty in separating by-produced glycine, etc. as reported in JP-A-63-51399 (the term "JP-A" used herein means an unexamined published Japanese patent application).

Further, it was also reported in Aust. J. Chem., 7, 173 (1954) that an N-chloroacetyl derivative of an amino acid is generally difficult to crystallize.

SUMMARY OF THE INVENTION

An object of the present invention is to provide a process for producing N-chloroacetylglutamine, an intermediate useful for producing glycylglutamine, with high purity at low cost from the industrial viewpoint, in which N-chloroacetylglutamine produced can be isolated and purified efficiently without complicated extraction.

The present invention relates to a process for producing N-chloroacetylglutamine represented by formula (I):

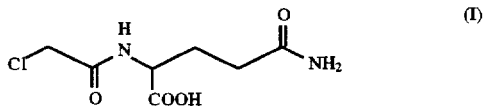 (I)

comprising reacting chloroacetyl chloride represented by formula (II):

 (II)

with an alkaline aqueous solution of glutamine in the presence of a water-immiscible organic solvent, separating an aqueous layer by liquid-liquid separation, and crystallizing N-chloroacetylglutamine from the aqueous layer under acidic conditions.

DETAILED DESCRIPTION OF THE INVENTION

The aqueous alkaline solution in which glutamine is to be dissolved is not particularly limited as long as the reaction is not hindered and includes an aqueous solution containing an inorganic base, such as sodium hydroxide, potassium hydroxide, lithium hydroxide, sodium carbonate or potassium carbonate, and an aqueous solution containing an organic base, such as trimethylamine, triethylamine or pyridine. Sodium hydroxide, potassium hydroxide, sodium carbonate and potassium carbonate are preferred alkalis.

The concentration of the glutamine to be employed in the aqueous alkaline solution may be from 0.01 to 3M, preferably from 0.1 to 1M.

The water-immiscible organic solvents include ether, toluene, chloroform, methylene chloride, dichloroethane, ethyl acetate, and mixtures thereof. Toluene, chloroform, and methylene chloride are preferred.

While not limiting, the organic solvent is used in an amount 0.1 to 5, preferably 0.3 to 1, times the volume of the alkaline aqueous solution of glutamine.

Since hydrochloric acid is formed with the progress of the reaction which reduces the pH of the reaction mixture, the reaction mixture is adjusted to a pH between 7 and 13, preferably between 10 and 12, during the reaction.

Glutamine is used in an amount usually of from 0.5 to 2.0 equivalents, preferably 1 equivalent, to chloroacetyl chloride.

The reaction is carried out at a temperature of $-5°$ to $40°$ C., preferably $0°$ to $10°$ C., for a period of 0.1 to 5 hours, preferably 0.5 to 2 hours.

In general, an acid halide is apt to be hydrolyzed and inactivated in an aqueous alkaline solution. In the present invention, since the acid halide exists in a water-immiscible organic solvent, it hardly undergoes any decomposition with an alkali, whereby the desired reaction proceeds on an interface between an aqueous alkaline solution layer and an organic solvent layer to achieve a high yield.

After completion of the reaction, the organic solvent is removed from the reaction mixture by liquid-liquid separation. The aqueous alkaline solution layer thus separated is adjusted to a pH of 0.1 to 3, preferably 1 to 2, with a strong acid, such as hydrochloric acid or sulfuric acid, and, after seeding, cooled to obtain crystals of crude N-chloroacetylglutamine in good yield.

Recrystallization of the resulting crude N-chloroacetylglutamine from water gives purified N-chloroacetylglutamine. Alternatively, the crude N-chloroacetylglutamine is suspended in an appropriate organic solvent or a mixed solvent of an organic solvent and water, the resulting suspension is stirred, an insoluble salt is removed by filtration, and the filtrate is subjected to recrystallization to obtain purified N-chloroacetylglutamine.

The organic solvent which can be used in the above-described purification procedure includes alcohols, such as methanol, ethanol and propanol, and acetone, with ethanol being preferred. The solvent is used in an amount of 0.5 to 10 times, preferably 1 to 5 times, the weight of the crude N-chloroacetylglutamine. The stirring and filtration are performed at a temperature of $5°$ to $50°$ C., preferably $30°$ to $40°$ C. The stirring is continued for 5 minutes to 3 hours, preferably 10 minutes to 1 hour.

If desired, the resulting pure N-chloroacetyl-glutamine can further be recrystallized from water to achieve higher purity.

The crude N-chloroacetylglutamine as referred to above may be reacted, without being purified, with an aqueous solution containing ammonia to afford glycylglutamine with high purity in high yield.

The present invention provides a process for producing N-chloroacetylglutamine useful as an intermediate for producing glycylglutamine, with high purity at low cost from the industrial viewpoint, in which N-chloroacetyl-glutamine produced can be isolated and purified efficiently without complicated extraction.

The present invention will now be illustrated in greater detail with reference to Examples and Reference Example, but it should be understood that the present invention is not deemed to be limited thereto.

EXAMPLE 1

Synthesis of N-Chloroacetyl-L-glutamine

To a mixed solvent of 1750 ml of water and 497 ml of toluene was added 733.7 g (5 mol) of L-glutamine at room temperature. The solution was cooled to 0° to 5° C. and adjusted to pH 11 with 5N sodium hydroxide. To the solution was added dropwise a solution of 565.3 g (5 mol) of chloro-acetyl chloride in 497 ml of toluene while maintaining the pH of the reaction mixture at 11 with 5N sodium hydroxide. After stirring at 0° to 5° C. for 1 hour, toluene was removed from the reaction mixture by liquid-liquid separation. The aqueous layer separated was adjusted to pH 2 by addition of 410 ml of concentrated hydrochloric acid. After seeding, the reaction mixture was subjected to crystallization at room temperature for 1 hour and then at 0° to 5° C. for 3 hours. The resulting crystals were collected by filtration and dried under reduced pressure to give 992.6 g (89.2 mole percent (mol %) yield) of crude N-chloroacetyl-L-glutamine (sodium chloride content: 13.6 weight percent (wt %)). The crystals were analyzed by high performance liquid chromatography (HPLC) (column: Shim-pack CLC-ODS, 6 ×150 mm (manufactured by Shimadzu Corporation); eluent: 0.01M sodium 1-octanesulfonate/ 0.01M $KH_2PO_4$ buffer (pH 2.5)/1% methanol; detection: UV 210 nm). The purity of the crystals was found to be 99.0% as calculated from the HPLC relative area ratio.

EXAMPLE 2

Purification of Crude N-Chloroacetyl-L-glutamine

Fifty grams of the crude N-chloroacetyl-L-glutamine obtained in Example 1 were dissolved in 100 ml of water by heating to 50° C. The resulting solution was gradually cooled to 0° to 5° C. and crystallized for 2 hours. The crystals thus precipitated were collected by filtration and dried under reduced pressure to recover 36.9 g (73.2 mol % yield) of N-chloroacetyl-L-glutamine (sodium chloride content: 3.1 wt %). As a result of HPLC under the same conditions as in Example 1, the purity of the resulting product as calculated from the HPLC relative area ratio was 99.4%.

Recrystallization of 25 g of the resulting N-chloroacetyl-L-glutamine from water gave 18.0 g (71.9 mol % yield) of highly pure N-chloroacetyl-L-glutamine (sodium chloride content: 0.7 wt %). As a result of HPLC under the same conditions as in Example 1, the purity of the resulting product as calculated from the HPLC relative area ratio was 99.7%.

EXAMPLE 3

Purification of Crude N-Chloroacetyl-L-glutamine

Fifty grams of the crude N-chloroacetyl-L-glutamine obtained in Example 1 were added to 250 ml of ethanol and heated to 40° C. The suspension was stirred at 45 minutes and filtered while hot at 40° C. The filtrate was concentrated under reduced pressure to remove ethanol. To the residue was added 20 ml of water, followed by heating to 50° C. to dissolve. The solution was slowly cooled to room temperature and, after seeding, further cooled to 0° to 5° C. to conduct crystallization for 2 hours. The resulting crystals were collected by filtration and dried under reduced pressure to obtain 14.2 g (28.3 mol % yield) of N-chloroacetyl-L-glutamine (sodium chloride content: 0.15 wt %). As a result of HPLC under the same conditions as in Example 1, the purity of the resulting product as calculated from the HPLC relative area ratio was 99.8%.

Then, 13 g of the N-chloroacetyl-L-glutamine was dissolved in 39 ml of water by heating at 55° C. The solution was gradually cooled to 0° to 5° C. and crystallized for 2 hours. The resulting crystals were collected by filtration and dried under reduced pressure to afford 9.4 g (71.9 mol % yield) of highly purified N-chloroacetyl-L-glutamine (sodium chloride content: 0.012 wt %). As a result of HPLC under the same conditions as in Example 1, the purity of the resulting product as calculated from the HPLC relative area ratio was 100%. The physicochemical properties of N-chloroacetyl-L-glutamine were as follows.

$^1$H-NMR (300MHz, DMSO-$d_6$) δ(ppm): 1.71–2.02 (2H, m), 2.12 (2H, t), 4.10 (2H, s), 4.13–4.21 (1H, m), 6.60 (1H, s), 7.31 (1H, s), 8.52 (1H, d), 11.99–13.32 (1H, m).

$^{13}$C-NMR (75.5MHz, DMSO-$d_6$) δ(ppm): 26.7, 31.1, 42.3, 51.9, 166.0, 172.9, 173.3.

MS (SIMS, m/z) for $C_7H_{11}{}^{35}ClN_2O_4$: 223 ($M^+$+1)

IR (KBr) cm$^{-1}$: 1538, 1588, 1640, 1662, 1734, 3350, 3450

Elementary Analysis for $C_7H_{11}ClN_2O_4$: Calcd. (%): C 37.77%; H 4.98%; N 12.58% Found (%): C 37.60%; H 4.84%; N 12.47%

$[\alpha]_D{}^{20}$=-8.59° (c=10, water)

Melting point: 135° C.

REFERENCE EXAMPLE

Synthesis of Glycyl-L-glutamine

To a mixed solvent of 250 ml of water and 2025 ml (30 mol) of 28% aqueous ammonia was added 1186.0 g (15 mol) of ammonium hydrogen carbonate at room temperature, followed by heating to 40° C. to form a solution. The solution was cooled to room temperature, and 386.0 g (1.5 mol) of crude N-chloroacetyl-L-glutamine as obtained in Example 1 was added thereto, followed by allowing the mixture to react at 40° C. for 8 hours. The reaction mixture was concentrated under reduced pressure, and 2050 ml of water was added to the residue, followed by concentration again. To the residue was added 650 ml of water to make the total weight 1162 g. Ten grams of activated carbon were added thereto, and the mixture was stirred at 50° C. for 30 minutes. The activated carbon was washed with 166 ml of water and filtered while hot. To the filtrate was added dropwise 550 ml of methanol at 50° C. After seeding, 550 ml of methanol was further added, followed by cooling to 0° to 5° C., at which crystallization was continued for 3 hours. The resulting crystals were collected by filtration and dried under reduced pressure to obtain 250.8 g (75.6 mol % yield) of glycyl-L-glutamine. As a result of HPLC under the same conditions as in Example 1, the purity of the resulting product as calculated from the HPLC relative area ratio was 97.2%.

While the invention has been described in detail and with reference to specific examples thereof, it will be apparent to one skilled in the art that various changes and modifications can be made therein without departing from the spirit and scope thereof.

What is claimed is:

1. A process for producing N-chloroacetylglutamine represented by formula (I):

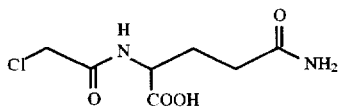 (I)

consisting the steps of:

(a) reacting chloroacetyl chloride represented by formula (II):

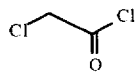 (II)

with an alkaline aqueous solution of glutamine in the presence of a water immiscible organic solvent;

(b) separating an aqueous layer by liquid-liquid separation; and (c) after seeding the aqueous layer crystallizing N-chloroacetylglutamine from said aqueous layer under acidic conditions.

* * * * *